United States Patent [19]

Joung

[11] 4,302,852
[45] Dec. 1, 1981

[54] HYPOALLERGENIC SLIP RESISTANT GLOVES AND METHODS OF MAKING SAME

[75] Inventor: John J. Joung, South Pasadena, Calif.

[73] Assignee: American Hospital Supply Corporation, Evanston, Ill.

[21] Appl. No.: 61,788

[22] Filed: Jul. 30, 1979

[51] Int. Cl.³ .................................... A41D 19/00
[52] U.S. Cl. .................................................. 2/167
[58] Field of Search ............... 2/167, 168, 164, 161 R, 2/159, 243 R; 428/447; 264/255, 306

[56] References Cited

U.S. PATENT DOCUMENTS

| Re. 24,953 | 3/1961 | Homeyer et al. | 428/447 X |
|---|---|---|---|
| 732,360 | 6/1903 | Lindsay | 2/168 |
| 2,668,789 | 2/1954 | Phreaner | 428/447 X |
| 2,781,288 | 2/1957 | Polmanteer | 428/447 |
| 2,789,933 | 4/1957 | Bargmeyer | 428/447 |
| 2,989,755 | 6/1961 | O'Brien et al. | 2/168 |
| 4,210,699 | 7/1980 | Schroeter et al. | 428/447 X |
| 4,218,513 | 8/1980 | Williams et al. | 428/447 X |

FOREIGN PATENT DOCUMENTS 682769 3/1964 Canada.

Primary Examiner—H. Hampton Hunter
Attorney, Agent, or Firm—Larry N. Barger; Donald L. Barbeau

[57] ABSTRACT

A hypoallergenic surgeon's glove with an allergenic elastomeric support glove, such as natural latex, has secured to its inner surface by covalent chemical bonds a barrier glove of a nonallergenic elastomer, such as silicone. Sharp angular flexing in the knuckle area, as well as stretching and snapping during donning, does not crack the barrier glove nor delaminate it from the support glove. This hypoallergenic glove requires only about ⅓ the amount of lubricating donning powder in a natural latex glove. In another example, a slip resistant glove, such as silicone, is secured by covalent chemical bonds to an external surface of the support glove.

30 Claims, 6 Drawing Figures

HYPOALLERGENIC SLIP RESISTANT GLOVES AND METHODS OF MAKING SAME

BACKGROUND

There have been many attempts to make laminated surgeon's gloves to alter the glove's surface properties. These have included slip coating layers for donning, hypoallergenic layers, and outer surface grip improving layers. However, to applicant's knowledge, none of these prior art laminated gloves have ever been marketed. This is believed to be caused by the very stringent requirements of a surgeon's glove, such as highly angular flexing in the knuckle area, and very large percentages of stretch and snapback during the donning procedure. Often the laminated layers could not withstand such harsh physical treatment without breaking down or delaminating.

U.S. Pat. No. 2,989,755 describes a hypoallergenic glove in which a rubber cement is coated on a latex glove. The rubber cement coating is described as blending or coalescing with the latex glove to form a somewhat adhesive or mechanical bond between the coating and latex glove. This patent is assigned to a very large surgeon glove manufacturer and technology has been available to them for more than 20 years. However, this hypoallergenic laminated glove has never been marketed.

Other attempts of laminating gloves which rely on adhesion at the interface include U.S. Pat. Nos. 4,070,713; 4,027,060; and 3,813,695. The latter polymerizes a hydrogel resin in place on a rubber surface in an effort to improve the interface bond. The hydrogel can absorb perspiration as well as lubricants.

U.S. Pat. No. 3,382,138 shows still another approach at surface modification of latex rubber articles for abrasion resistance. Here a polyurethane elastomer is dispersed in a coagulant solution for latex and a layer of latex and polyurethane are "codeposited" on a surface of a latex rubber article, such as a girdle, glove, swim suit, etc. Because of the codeposition, the polyurethane does not form an outer boundary layer for the rubber latex. The rubber latex, as well as its allergenic components, would still be available at the surface of the rubber article. The latex and polyurethane would be blended at the surface in a manner similar to the structure of automobile tires where abrasion resistant materials, such as clay, etc., are compounded with the rubber prior to forming the tire.

Attempts have also been made to produce a surgeon's glove made completely of silicone, as described in U.S. Pat. No. 3,872,515. A glove made completely of silicone would not be able to withstand the very strenuous stretching and snapping during donning, as well as sharp angular flexure in the knuckle area, without dimensional change during use. Dimensional change or elasticity modification during a tedious surgical procedure is highly undesirable. In addition, an all silicone surgeon's glove is very expensive due to the cost of silicone rubber.

In a different field of urine drainage, it has been proposed to chemically bond a silicone elastomer layer to a rubber latex Foley catheter. A Foley catheter includes a tube which has an inflatable balloon near one end which is inflated in a patient's bladder after insertion of the Foley catheter through the urethra. The balloon forms a knob on the catheter end to prevent the Foley catheter from prematurely being pulled from the urethra. Because of the structure of the Foley catheter, it would be impossible to coat an inner surface of the balloon with silicone. A Foley catheter balloon is usually inflated only once and maintains a static, generally spherical shape, while in the patient. Stretching forces on the balloon are approximately equal in all directions. The balloon is also deflated only once at the time of removal.

In addition to being in separate fields, a surgeon's glove has totally different physical requirements from a Foley catheter balloon. For instance, a surgeon's glove is subjected to very strenuous stretching, pulling, and snapping during the donning procedure. The stretch forces are applied in many different directions and in varying degrees of stretch. During surgery, the knuckle area of a surgeon's glove is under continual sharp angular flexing and unflexing. With continual flexing and movement of the hand inside the glove, and perhaps some slight movement of the hand relative to the glove, certain physicians experience irritation on the skin of their hands. They develop an allergy or sensitivity to certain biological components of natural rubber, sulphur and other accelerators and preservative components of rubber latex. In addition, some physicians find that the exterior surface of rubber latex surgeon's gloves are more slippery than desired, particularly when handling instruments under wet surgical conditions.

SUMMARY OF THE INVENTION

This invention has overcome the problems explained above by providing a surgeon's glove which withstands all of the rigors required during donning and use, and which can still be hypoallergenic. This glove includes a supporting glove of an elastomer containing an allergenic material which has secured to its inner surface by covalent chemical bonds an inner barrier glove of a nonallergenic elastomer. A glove is also provided which has a support glove of a first elastomer and secured to an outer surface by covalent chemical bonds is a slip resistant outer glove of a different elastomer. The process of making the surgeon's glove includes attaching the barrier glove to the support glove and bonding the two gloves by covalent chemical bonds and thereafter curing the barrier glove. During this process, a lubricating donning powder in an amount substantially less (approximately ½) than required for a rubber latex glove is applied.

THE DRAWINGS

DETAILED DESCRIPTION

Figure 1:
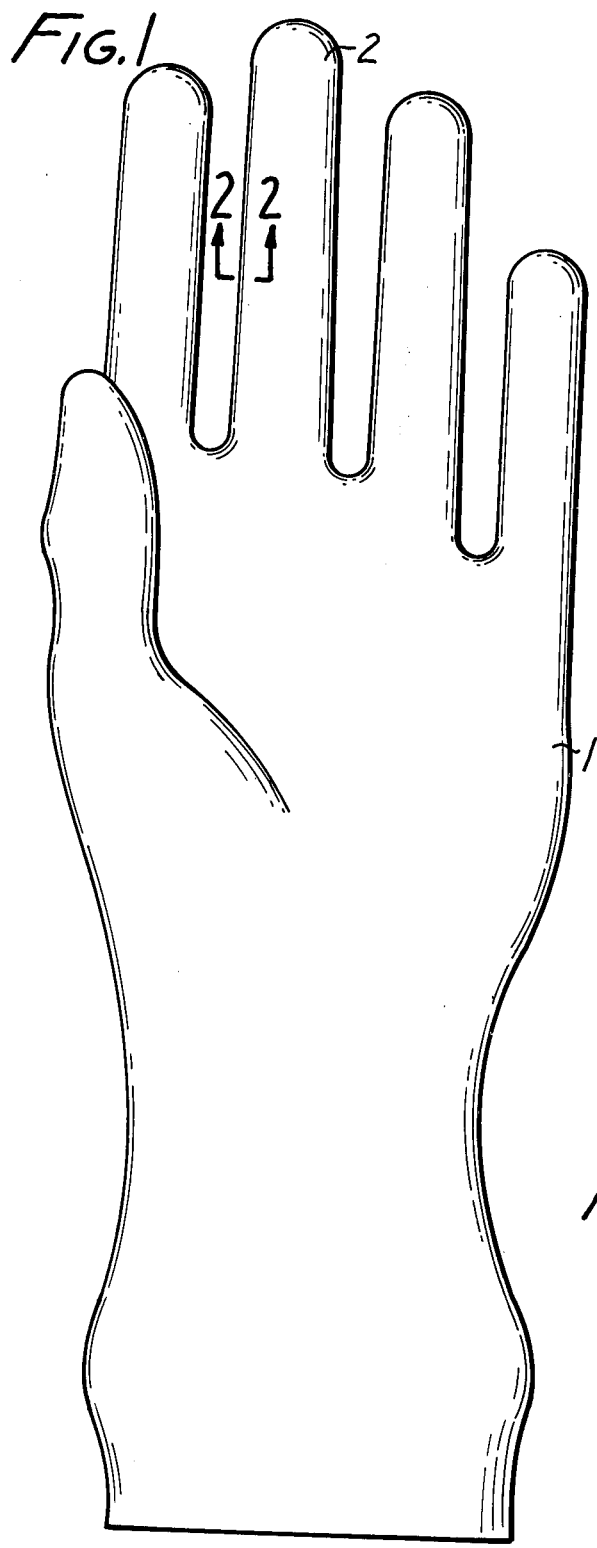
FIG. 1 is a front elevational view of a surgeon's glove.

FIG. 1 shows a surgeon's glove 1 with a thumb and fingers, one of which is designated as 2. The enlarged sectional view taken along line 2—2 of finger shows a schematic drawing of a wall section of this surgeon's glove. Here a support glove 3 is formed of an elastomeric material, such as natural rubber latex. For the proper elasticity and tensile strength, support glove 3 must contain vulcanizing agents including sulphur, accelerators, and preservatives which some physicians find irritating to the skin of their hands. This is particularly true of surgeon's gloves which are constantly flexing and exerting a compression force against the hand.

An inner barrier glove 4 of a nonallergenic elastomer is secured by covalent chemical bonds to an inner surface of support glove 3. This barrier glove can be of a Room Temperature Vulcanizing (RTV) silicone. Such silicones are very inert relative to tissue irritability. Because both the support and barrier gloves are elastomers, chemically bonding them together does not substantially alter the overall stretch and return characteristics of the glove. Also, since the support glove is the main body structure of the surgeon's glove, it is important that the barrier glove has an equal or greater elongation than the support glove so that upon extreme stretching, the barrier glove does not craze or discolor when highly stretched during use, particularly in the knuckle area. The support glove can have a thickness range of 0.003 to 0.10 inch, and the barrier glove can have a thickness in the range of 0.0002 to 0.002 inch.

Figure 2:
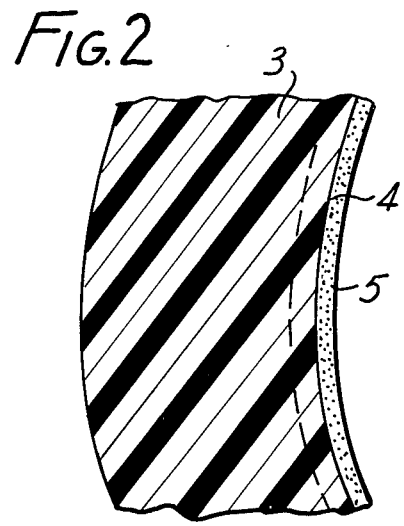
FIG. 2 is an enlarged sectional view taken along line 2—2 of FIG. 1 showing the hypoallergenic glove.

It is common practice with a surgeon's natural latex glove to use a lubricating dusting powder, such as starch, on an inner surface to overcome the glove's natural tackiness and prevent easy donning. RTV silicones have a certain tackiness to them also. Thus, it would be expected that at least as much lubricating donning powder would be needed for the barrier glove of silicone as was needed for the natural latex glove. However, it was unexpectedly discovered that substantially less lubricating powder was needed with the silicone barrier glove. In FIG. 2, the lubricating donning powder is shown schematically at 5. It is important to use as little as possible lubricating powder to substantially reduce the chance of any such powder entering the surgical wound.

Figure 3:
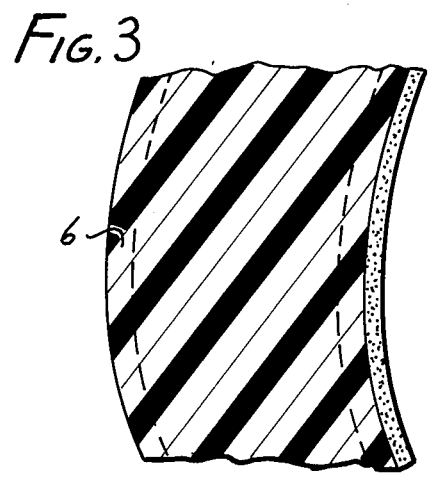
FIG. 3 is a view similar to FIG. 2, but showing an embodiment that includes an external slip resistant glove.

FIG. 3 shows another embodiment of the invention similar to FIG. 2, however, with the addition of an outer slip resistant glove 6 secured to the supporting glove by covalent chemical bonds. This slip resistant glove can be of the same elastomer as barrier glove 4; i.e., RTV silicone. It has been unexpectedly found in the FIG. 3 embodiment that an RTV silicone combined with very light lubricating powder gives an equivalent or superior slippery surface for donning as with previous rubber latex gloves. However, this same silicone glove on an outer surface of the support glove provides increased slip resistance over natural latex gloves. External slip resistance is important in handling delicate surgical instruments, particularly in a wet surgical sight.

Figure 4:
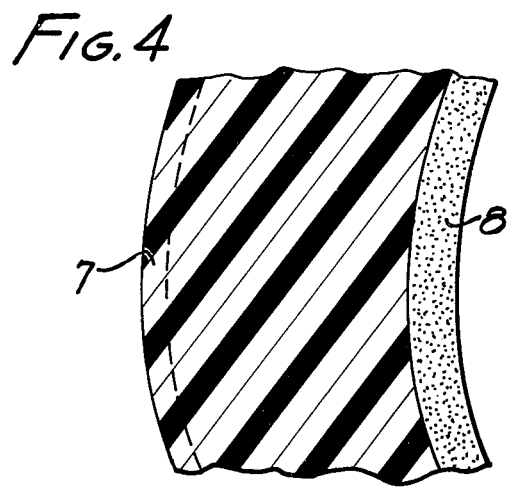
FIG. 4 is a view similar to FIG. 2, but showing still another embodiment with the outer slip resistant glove, but without the inner hypoallergenic barrier glove.

FIG. 4 is yet another embodiment in which a slip resistant glove is covalently bonded to an external surface of the support glove which does not have an inner barrier glove. Instead, a lubricating donning powder is used in an amount normally used with natural latex gloves. The difference in donning powder is shown schematically by layer thickness. However, it is understood that the thickness ratios between the various elements in FIGS. 2-4 have been exaggerated for clarification.

Figure 5:
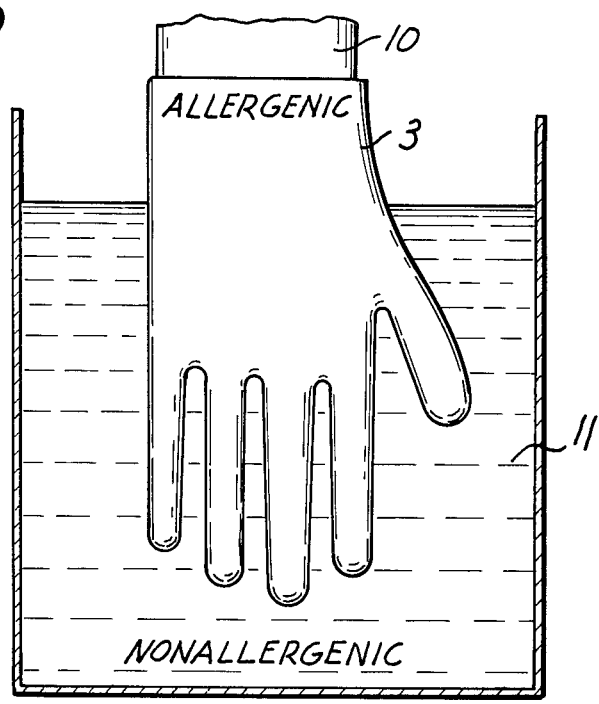
FIG. 5 is a schematic view showing a forming step in making the glove embodiment shown in FIG. 2.
Figure 6:
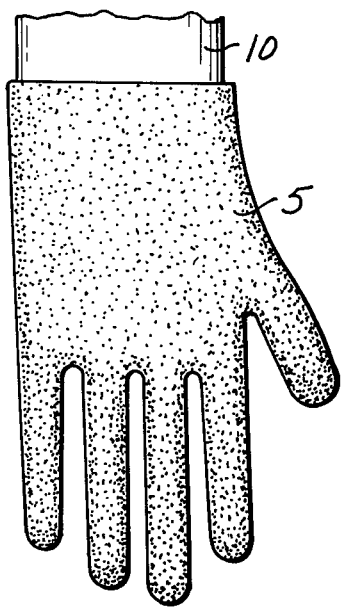
FIG. 6 is a schematic view showing the glove of FIG. 2 with lubricating donning powder applied.

FIGS. 5 and 6 schematically show two of the steps in forming the hypoallergenic glove of FIG. 2. In FIG. 5, glove 3 of an allergenic elastomer is carried on glove form 10 and attached to the nonallergenic barrier glove by dipping. The two gloves are bonded together by covalent chemical bonds, and the barrier glove is secured by steam treatment at 150°-230° F. for a period of 3-20 minutes. Then a very thin coating of lubricating donning starch, shown in FIG. 6, is applied to the glove. The glove is then stripped from the form 10 and everted so the powder 5 is inside the surgeon's glove.

EXAMPLE 1

A ceramic glove form was preheated to 150° F. and through coagulant and latex dipping processes, as is wellknown in the glove art, the latex glove of coagulum was deposited on the form. After air drying for 2-3 minutes, all soluble components in the coagulant, as well as the latex, were dissolved in running water for 8 minutes. The dry coagulum on the glove form was cured at 260° F. for 20 minutes. The glove while still on the form was subjected to forced air cooling, until the temperature became 160° F.

The form was momentarily dipped into a priming solution composed of a sulfhydryl-alkylethoxysilane in isopropanol as disclosed in U.S. Pat. No. 3,434,869. The primed glove was then dipped in an RTV silicone coating and cured. The glove was then lightly coated with a lubricating donning powder and then stripped from the glove form everting the glove so the powder was inside the surgeon's glove.

EXAMPLE 2

A similar procedure according to Example 1, except the primer and silicone are applied in a single step. In the present example, ½ liter of 3% 3-mercaptopropyl-triethoxy-silane in isopropanol was added to 5 liters of 8% acetoxy-polydimethylsiloxane in petroleum ether containing a small amount of fumed silica and the mixture stirred well. If desired, fumed silica could be eliminated. The unstripped gloves were dipped into the solution after they were cooled to 150° F. When most of the solvent evaporated, the gloves were heated with steam at 210° F. for 5-10 minutes. The gloves were cooled in a cold air stream and then coated with powder and stripped from the form. The silicone layer was cured and did not delaminate or craze even when exhaustive repetitive stretching and releasing occurred. The prepared gloves were sent to surgeons that were known to be allergenic to the conventional rubber latex surgeon's gloves. The surgeons could wear the gloves of this invention without irritation.

The repeated sharp angular flexing in the knuckle area, as well as stretching and snapping during donning, did not interrupt the barrier layer against the surgeon's hand. This is because of the covalent chemical bond between the barrier glove and the support glove. The natural rubber latex of the support glove has vinyl groups which accept a hydrogen from the sulfhydryl or epoxy group of the linking (primer) silane, causing the sulphur molecules or epoxy carbon to form a covalent chemical bond with the latex vinyl group.

The linking silane also has an ethoxy or hydroxy unit that reacts with an acetoxy unit of the silicone barrier glove in the presence of moisture to release acetic acid and covalently bond the silicone directly to the silane linker (primer). Other linking structure and mechanisms could be used, so long as there is a direct covalent chemical bond between the barrier glove and the support glove. The present glove does not require adhesion or mechanical interlock between pore structure, etc. at the interface between the support and barrier glove which caused the problems with prior art laminated surgeon's gloves.

Other allergenic, nonallergenic, and slip resistant elastomers can be used so long as they meet the general spirit of the present invention. For instance, synthetic as well as natural latex could be used for the support glove and to provide the vinyl groups. Also, the polyurethane with hydroxy groups could be covalently bonded to an isocyanate linker to provide an inner barrier glove of polyurethane.

While specific embodiments have been used to illustrate the invention, it is understood that those skilled in the art can make certain modifications to these embodiments without departing from the spirit and scope of the invention.

I claim:

1. A hypoallergenic surgeon's glove comprising: an outer support glove of a first elastomer containing an allergenic material; an inner barrier glove of a second non-allergenic elastomer secured by covalent chemical bonds to an inner surface of the support glove, wherein the inner barrier glove requires an amount of lubricating donning powder substantially less than that for donning a glove of the first elastomer, whereby sharp angular flexing in the knuckle area, as well as stretching and snapping during donning, does not delaminate the gloves nor interfere with the barrier glove's isolation of allergenic material from a surgeon's hand.

2. A surgeon's glove as set forth in claim 1, wherein the barrier glove has an inner surface coated with a lubricating donning powder in an amount substantially less then required for donning a glove of the first elastomer.

3. A surgeon's glove as set forth in claim 1, wherein the powder is starch and approximately ⅓ the amount of powder is required.

4. A surgeon's glove as set forth in claim 1, wherein the first elastomer is latex rubber.

5. A surgeon's glove as set forth in claim 1, wherein the second elastomer is silicone.

6. A surgeon's glove as set forth in claim 1, wherein the second elastomer is capable of stretching as much or more than the first elastomer to prevent crazing in the knuckle area.

7. A surgeon's glove as set forth in claim 1, wherein the support glove has a thickness of 0.003 to 0.010 inch and the barrier glove has a thickness of 0.0002 to 0.002 inch.

8. A surgeon's glove as set forth in claim 1, wherein the support glove has secured to its outer surface by covalent chemical bonds a slip resistant glove of an elastomer different than the first elastomer.

9. A surgeon's glove as set forth in claim 8, wherein the slip resistant glove and barrier glove are the same elastomer.

10. A surgeon's glove as set forth in claim 9, wherein both are silicone.

11. A surgeon's glove as set forth in claim 8, wherein the slip resistant glove elastomer is capable of stretching as much or more than the first elastomer to prevent crazing in the knuckle area.

12. A method of making a hypoallergenic surgeon's glove comprising the steps of:

(a) forming a support glove of a first elastomer containing an allergenic material;
(b) attaching a barrier glove of a second non-allergenic elastomer to an exterior of the support glove, wherein the barrier glove requires an amount of lubricating donning powder substantially less than that for donning a glove of the first elastomer;
(c) bonding the two gloves together by covalent chemical bonds;
(d) curing the barrier glove; and
(e) everting the two gloves so that the barrier glove is inside the support glove, whereby sharp angular flexing in the knuckle area, as well as stretching and snapping during donning, does not delaminate the glove nor interfere with the barrier glove's isolation of allergenic material from a surgeon's hand.

13. A method as set forth in claim 12, wherein the curing step includes a steam treatment.

14. A method as set forth in claim 13, wherein the steam treatment is at 150°–230° F. and continues for a period of 3–20 minutes.

15. A method as set forth in claim 12, wherein the first elastomer is latex.

16. A method as set forth in claim 12, wherein the second elastomer is silicone.

17. A method as set forth in claim 12, wherein the method also includes applying to the barrier glove, prior to everting, a lubricating donning powder in an amount substantially less than required for donning a glove of the first elastomer.

18. A method as set forth in claim 17, wherein the powder is starch and approximately ⅓ the amount of powder is required.

19. A method as set forth in claim 12, wherein the method also includes attaching to an outer surface of the support glove a slip resistant glove of an elastomer different than the first elastomer; bonding the slip resistant glove and support glove together by covalent chemical bonds; and curing the slip resistant glove.

20. A slip resistant surgeon's glove comprising: a support glove of a first elastomer; a slip resistant glove of a different elastomer secured to an outer surface of the support glove by covalent chemical bonds, whereby sharp angular flexure in the knuckle area, as well as stretching and snapping during donning, do not delaminate the two gloves nor interfere with the properties of the slip resistant glove.

21. A surgeon's glove as set forth in claim 20, wherein the support glove is latex.

22. A surgeon's glove as set forth in claim 20, wherein the slip resistant glove is silicone.

23. A surgeon's glove as set forth in claim 20, wherein the slip resistant elastomer is capable of stretching as much or more than the first elastomer to prevent crazing in the knuckle area.

24. A method of making a slip resistant surgeon's glove comprising the steps of:

(a) forming a support glove of a first elastomer;
(b) attaching a barrier glove of a second elastomer to an exterior of the support glove, said second elastomer having greater resistance to surface slipping than the first elastomer when in contact with surgical instruments in a wet surgical site;
(c) bonding the two gloves together by covalent chemical bonds;
(d) curing the barrier glove; and (e) arranging the glove for donning so that the barrier glove is on an external surface of the surgeon's glove.

25. A method as set forth in claim 24, wherein the surgeon's glove is made on a form with the barrier glove as the external glove, and the arranging step includes: stripping the surgeon's glove from such mold by an everting action that causes the barrier glove to become the interior glove; and thereafter reverting the surgeon's glove causing the barrier glove to be the exterior glove after the surgeon's glove is donned.

26. A method as set forth in claim 24, wherein the curing step includes a steam treatment.

27. A method as set forth in claim 24, wherein the steam treatment is at 150°-230° F. and continues for a period of 3-20 minutes.

28. A method as set forth in claim 24, wherein the first elastomer is latex.

29. A method as set forth in claim 24, wherein the second elastomer is silicone.

30. A method of reducing the amount of lubricating powder required on a surgeon's glove comprising: chemically securing a barrier glove of silicone elastomer to an outer support glove of a first elastomer containing an allergenic material, whereby sharp angular flexing in the knuckle area, as well as stretching and snapping during donning, does not delaminate the gloves nor interfere with the barrier glove's isolation of allergenic material from a surgeon's hand.

* * * * *